United States Patent
Cheng et al.

(10) Patent No.: US 9,329,180 B2
(45) Date of Patent: May 3, 2016

(54) PREPARATION OF ANTI-PEG ANTIBODY EXPRESSING CELL AND APPLICATION THEREOF

(71) Applicant: KAOHSIUNG MEDICAL UNIVERSITY, Kaohsiung (TW)

(72) Inventors: Tian-Lu Cheng, Kaohsiung (TW); Steven R. Roffler, Kaohsiung (TW); Kuo-Hsiang Chuang, Kaohsiung (TW); Ssu-Jung Lu, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 242 days.

(21) Appl. No.: 14/057,999

(22) Filed: Oct. 18, 2013

(65) Prior Publication Data

US 2014/0038208 A1 Feb. 6, 2014

Related U.S. Application Data

(63) Continuation-in-part of application No. 13/032,317, filed on Feb. 22, 2011, now abandoned.

(30) Foreign Application Priority Data

Jul. 19, 2010 (TW) .............................. 099123699 A (51) Int. Cl.
| | |
|---|---|
| G01N 33/53 | (2006.01) |
| G01N 33/554 | (2006.01) |
| G01N 33/68 | (2006.01) |
| G01N 33/94 | (2006.01) |
| C07K 16/44 | (2006.01) |

(52) U.S. Cl.
CPC .............. *G01N 33/554* (2013.01); *C07K 16/44* (2013.01); *G01N 33/5308* (2013.01); *G01N 33/6857* (2013.01); *G01N 33/94* (2013.01); *G01N 33/9493* (2013.01); *C07K 2317/56* (2013.01); *C07K 2319/03* (2013.01); *C12N 2503/02* (2013.01); *C12N 2510/04* (2013.01); *G01N 2430/60* (2013.01); *G01N 2440/28* (2013.01)

(58) Field of Classification Search
CPC .............. C07K 16/44; C07K 2317/56; C07K 2319/03; C12N 2503/02; C12N 2510/04; G01N 33/5308; G01N 33/554; G01N 33/6857; G01N 33/94; G01N 33/9493; G01N 2430/60; G01N 2440/28
See application file for complete search history.

(56) References Cited

U.S. PATENT DOCUMENTS

| | | | | |
|---|---|---|---|---|
| 6,596,849 | B1 * | 7/2003 | Roffler | G01N 33/5308 435/7.1 |
| 8,227,199 | B2 * | 7/2012 | Urech | C07K 16/22 435/40.51 |
| 8,507,207 | B2 * | 8/2013 | Cheng | A61K 49/0019 435/320.1 |
| 2003/0017504 | A1 * | 1/2003 | Roberts | C07K 16/44 435/7.1 |
| 2011/0064651 | A1 * | 3/2011 | Cheng | A61K 49/0019 424/1.11 |

OTHER PUBLICATIONS

Chen et al., 1996. A quantitative immunoassay utilizing *Escherichia coli* cells possessing surface-expressed single chain Fv molecules. Biotechnol. Prog. 12: 572-574.*
Cheng et al., 2005. Monoclonal antibody-based quantitation of poly-(ethylene glycol)-derivatized proteins, liposomes, and nanoparticles. Bioconjugate Chem. 16(5): 1225-1231.*
Chuang et al., Mar. 15, 2010 (published on the Web on Feb. 23, 2010). Measurement of poly(ethylene glycol) by cell-based anti-poly(ethylene glycol) ELISA. Analytical Chemistry 82(6): 2355-2362.*
Huang et al., 2007. "The application of surface anti-polyethylene glycol antibody in biomedical research" and translation thereof.*
Armstrong, 2009. "The occurrence, induction, specificity and potentail effect of antibodies against poly(ethylene glycol)" in PEGylated Protein Drugs: Basic Science and Clinical Applications (F.M. Veronese, ed.), Birkhauser, Basel, pp. 147-168.*
Frykman et al., 1998. Quantitating secretion rates of individual cells: design of secretion assays. Biotechnol. Bioeng. 59: 214-226.*
Liu et al., 2010. "Development of an Optimal ELISA Kit for the Quantification of PEGlylated Molecules" and translation thereof.*
Su et al., 2010 (published on the Web on Jun. 10, 2010). Sensitive quantification of PEGylated compounds by second-generation anti-poly(ethylene glycol) monoclonal antibodies. Bioconjugate Chem. 21: 1264-1270.*

* cited by examiner

*Primary Examiner* — Gail R Gabel
*Assistant Examiner* — James L Grun
(74) *Attorney, Agent, or Firm* — Hannah M. Tien (57) ABSTRACT

The present invention provides a method for preparing an isolated eukaryotic cell which presents an anti-polyethylene glycol (PEG) antibody on a cell membrane. The present invention also provides a method for a quantitative analysis of a polyethylene glycol (PEG) by said anti-PEG antibody expressing cell. The cell-based quantitative analysis of the present prevention could sensitively quantify free PEG and PEG-modified macromolecules (proteins, nanoparticles and liposomes) as sensitive as nano-gram level.

15 Claims, 9 Drawing Sheets

FIG. 9

SEQUENCE LISTING

```
<160> NUMBER OF SEQ ID NOS: 10

<210> SEQ ID NO 1
<211> LENGTH: 348
<212> TYPE: DNA
<213> ORGANISM: Artificial
<220> FEATURE:
<223> OTHER INFORMATION: VH domain of AGP3 antibody
<220> FEATURE:
<221> NAME/KEY: V_region
<222> LOCATION: (1)..(348)
```

<400> SEQUENCE: 1

| | |
|---|---|
| gaagtgcagc tggtggagtc tgggggaggc ttagtgaagc ctggagggtc cctgaaactc | 60 |
| tcctgtgcag cctctggatt cactttcagt gactattaca tgtattgggt tcgccagact | 120 |
| ccggaaaaga ggctggagtg ggtcgcaacc attagtgatg atggtactta cacctactat | 180 |
| ccacacagtg tgaaggggcg attcaccatc tccagagaca gtgccaagaa caacctgtac | 240 |
| ctgcaattga gcagtctgaa gtctgaggac acagccatgt attactgtgc aagaaatgat | 300 |
| gctaggggg actactgggg tcaaggaacc tcagtcaccg tctcctca | 348 |

<210> SEQ ID NO 2
<211> LENGTH: 336
<212> TYPE: DNA
<213> ORGANISM: Artificial
<220> FEATURE:
<223> OTHER INFORMATION: VL domain of AGP3 antibody
<220> FEATURE:
<221> NAME/KEY: V_region
<222> LOCATION: (1)..(336)

<400> SEQUENCE: 2

| | |
|---|---|
| gatattgtgt tgacgcaggc tgcattctcc aatccagtca ctcttggaac atcagcttcc | 60 |
| atctcctgca ggtctagtaa gagtctccta catagtaatg gcatcactta tttgtattgg | 120 |
| tatctgcaga agccaggcca gtctcctcag ctcctgattt atcagatgtc caaccttgcc | 180 |
| tcaggagtcc cagacaggtt cagtagcagt gggtcaggaa ctgatttcac actgagaatc | 240 |
| agcagagtgg aggctgagga tgtgggtgtt tattactgtg ctcaaaatct agaactattc | 300 |
| acgttcggct cggggacaaa gttggaaata aaacgg | 336 |

<210> SEQ ID NO 3
<211> LENGTH: 357
<212> TYPE: DNA
<213> ORGANISM: Artificial
<220> FEATURE:
<223> OTHER INFORMATION: VH domain of E11 antibody
<220> FEATURE:
<221> NAME/KEY: V_region
<222> LOCATION: (1)..(357)

<400> SEQUENCE: 3

| | |
|---|---|
| caggtgcagc tgcaggagtc cggagctgaa ctggcaagac ctggggcctc agtgatgatg | 60 |
| tcctgcaagg cttctggcta cacctttact acctacacga tgaactgggt aaaacagagg | 120 |
| cctggacagg gtctggaatg gattggatac attattccta gcagtgggta tgttgactac | 180 |
| aatcagaagt tcaagggaaa gaccatattg actacagaca atcctccag cacagcctac | 240 |
| atgcaactga gcagcctgac atctgaggac tctgcggtct attactgtgt aagatcgctt | 300 |
| gatggttatt tctggtttgc ttactgggc caagggactc tggtcactgt ctctgca | 357 |

<210> SEQ ID NO 4
<211> LENGTH: 339
<212> TYPE: DNA
<213> ORGANISM: Artificial
<220> FEATURE:
<223> OTHER INFORMATION: VL domain of E11 antibody
<220> FEATURE:
<221> NAME/KEY: V_region
<222> LOCATION: (1)..(339)

<400> SEQUENCE: 4

| | |
|---|---|
| gatgttttga tgacccaaag tccactctcc ctgcctgtca gtcttggaga tcacgcgtcc | 60 |

| | |
|---|---|
| atctcttgca gatcaagtaa gagcattgta cacagtaatg gaaacaccta tttggaatgg | 120 |
| ttcctgcaga aaccaggcca gtctccaaaa ctcctgatct acaaagtttc caagcgaatg | 180 |
| tctggggtcc cagacaggtt cagtggcagt ggatcaggga cagatttcac actcaagatc | 240 |
| cgcagagtgg aggctgagga tctgggagtt tattactgct ctcaaggttc acatgttcct | 300 |
| cccacgttcg gagggggggac caaactggaa ataaaacgg | 339 |

<210> SEQ ID NO 5
<211> LENGTH: 354
<212> TYPE: DNA
<213> ORGANISM: Artificial
<220> FEATURE:
<223> OTHER INFORMATION: VH domain of 3-3 antibody
<220> FEATURE:
<221> NAME/KEY: V_region
<222> LOCATION: (1)..(354)

<400> SEQUENCE: 5

| | |
|---|---|
| gaagtcaagc tggaggagtc tggaggaggc ttggtgcaac ctggaggatc catgaaactc | 60 |
| tcttgtgctg cctctggatt cattttagt gacgcctgga tggactgggt ccgccagtct | 120 |
| ccagagaggg ggcttgagtg ggttgctgaa attagaagca aagctaatgg tcttgcacca | 180 |
| tactatgctg agtctgtgaa agggaggttc accatctcaa gagatgattc caaaagtagt | 240 |
| gtctacctgc aaatgaacaa cttaagatct gaagacactg gcatttatta ctgtacctct | 300 |
| actttgtatt actttgacta ctggggccaa ggcaccacgc tcacagtctc ctca | 354 |

<210> SEQ ID NO 6
<211> LENGTH: 327
<212> TYPE: DNA
<213> ORGANISM: Artificial
<220> FEATURE:
<223> OTHER INFORMATION: VL domain of 3-3 antibody
<220> FEATURE:
<221> NAME/KEY: V_region
<222> LOCATION: (1)..(327)

<400> SEQUENCE: 6

| | |
|---|---|
| cagattgtgc tcacacagtc tccagcaatc atgtctgcat ttcctgggga gagggtcacc | 60 |
| ttgacctgca gtgccagctc gagtgtgagg tccagctact tgtgctggta ccagcagaag | 120 |
| ccaggatcct cccccaaact ctggatttat agcacttcca acctggcttc tggagtccct | 180 |
| gctcgcttca gtggcagtgg gtctgggacc tcttactctc tcacaatcag cagcatggag | 240 |
| gctgaagatg ctgcctctta tttctgccat cagtggagta gttacccacg gacgttcggt | 300 |
| ggaggcacca agctggaaat caaacgg | 327 |

<210> SEQ ID NO 7
<211> LENGTH: 342
<212> TYPE: DNA
<213> ORGANISM: Artificial
<220> FEATURE:
<223> OTHER INFORMATION: VH domain of 6-3 antibody
<220> FEATURE:
<221> NAME/KEY: V_region
<222> LOCATION: (1)..(342)

<400> SEQUENCE: 7

| | |
|---|---|
| cagatccagt tggtgcagtc tggacctgag ctgaagaagc ctggagagac agtcaagata | 60 |
| tcctgcaagg cttctgggta cactttcaaa aactatggaa tgaactgggt gaagcaggct | 120 |
| ccaggaaagg gtttaaagtg gatgggctgg ataaacacct acactggaca gccaatatat | 180 |

-continued

| | |
|---|---|
| gctaatgact tcaagggacg gtttgccttc tctttggaaa cctctgccag cactgcctat | 240 |
| ttgcagatca acaacctcaa aaatgaggac acggctacat atttctgtgc aagagactgg | 300 |
| ggaccttact ggggccaagg gactctggtc attgtctctg ca | 342 |

<210> SEQ ID NO 8
<211> LENGTH: 339
<212> TYPE: DNA
<213> ORGANISM: Artificial
<220> FEATURE:
<223> OTHER INFORMATION: VL domain of 6-3 antibody
<220> FEATURE:
<221> NAME/KEY: V_region
<222> LOCATION: (1)..(339)

<400> SEQUENCE: 8

| | |
|---|---|
| aacattatga tgacccagtc tccatcatct ctggctgttt ctgcaggaga aaaggtcact | 60 |
| gtgaactgta agtccagtca agtgttttta tacagttcaa atcagatgaa ctacttggcc | 120 |
| tggtaccagc agaaaccagg acagtctcct aaactgctga tctactgggc atccactagg | 180 |
| gaatctggtg tccctgatcg cttcacaggc agtggatctg ggacagattt tactcttacc | 240 |
| atcagcagtg tacaaactga agacctggca gtttattact gtcttcaata cctctcctcg | 300 |
| tggacgttcg gtggaggcac caagctggaa atcaaacgg | 339 |

<210> SEQ ID NO 9
<211> LENGTH: 342
<212> TYPE: DNA
<213> ORGANISM: Artificial
<220> FEATURE:
<223> OTHER INFORMATION: VH domain of 15-2 antibody
<220> FEATURE:
<221> NAME/KEY: V_region
<222> LOCATION: (1)..(342)

<400> SEQUENCE: 9

| | |
|---|---|
| gaggttaagc tggaggagtc tggaggaggc ttggtgcaac ctggaggatc catgaaactc | 60 |
| tcctgtgttg cctctggatt cactttcagt aactactgga tgaactgggt ccgccagtct | 120 |
| ccagagaagg ggcttgagtg ggttactgaa attagatcga aatctaataa ttatgcgaca | 180 |
| cattatgcgg agtctgtgaa agggaggttc accatctcaa gagatgattc caaaggtagt | 240 |
| gtctacctgc aaatgaacaa cttaagagct gaagacactg gcatttatta ctgttccaac | 300 |
| agatactact ggggccaagg taccctggtc actgtctctg ca | 342 |

<210> SEQ ID NO 10
<211> LENGTH: 324
<212> TYPE: DNA
<213> ORGANISM: Artificial
<220> FEATURE:
<223> OTHER INFORMATION: VL domain of 15-2 antibody
<220> FEATURE:
<221> NAME/KEY: V_region
<222> LOCATION: (1)..(324)

<400> SEQUENCE: 10

| | |
|---|---|
| gacattgtga tgacacagtc tcacaaattc atgtccacat cagtacgaga cagggtcacc | 60 |
| atcacctgca aggccagtca ggatgtaaat acttctgtag cctggtatca acagaaacca | 120 |
| gggcaatctc ctaagctggt gatttattgg gcatccaccc ggcacactgg agtccctgat | 180 |
| cgcttcacag gcagtggatc tgggacagat ttcactctca ccattagcaa tgttcagtct | 240 |

```
gaagacttgg cagattattt ctgtctgcaa tatatcaact atccgtacac gttcggaggg    300
gggaccaagc tggaaataaa acgg                                           324
```

PREPARATION OF ANTI-PEG ANTIBODY EXPRESSING CELL AND APPLICATION THEREOF

CROSS-REFERENCE TO RELATED APPLICATIONS

This application is a Continuation-in-part of the pending U.S. patent application Ser. No. 13/032,317 filed on Feb. 22, 2011, for which priority is claimed and is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the prior art of record and any search that the Office deems appropriate.

FIELD OF THE INVENTION

The present invention relates to a method of preparing an isolated eukaryotic cell which presents an anti-polyethylene glycol (PEG) antibody on a cell membrane. In particular, the present invention provides a preparation of the anti-PEG antibody expressing cell and a cell-based assay useful for quantifying PEG.

BACKGROUND OF THE INVENTION

Polyethylene glycol (PEG) is a water-soluble, nontoxic, low immunogenic and biocompatible polymer that has been approved by the FDA for human usage by oral intake or intravenous and subcutaneous injection. Research shows that PEG has effects on preventing the colorectal cancer and healing the neuronal injury. Besides, the macromolecules (such as protein, nano drug and liposome) modified by PEG have the advantages on decreasing their immunogenicity, increasing half-life and biocompatibility. However, there is still no convenient way to effectively quantify PEG or PEG-modified (PEGylated) molecules in vivo.

Current methods used for quantifying PEG include, for example: (a) using the traditional ELISA, also known as the Sandwich Enzyme-Linked Immunosorbent Assay, to directly recognize protein, but the detecting process is hard to be achieved and the results are not precise due to the PEG used to modify proteins often cover the epitope for antibodies to recognize. Moreover, using ascites to produce antibodies has been prohibited by the European Union and the US, and this results the price of products related to ELISA to raise in the future. (b) A colorimetry which use barium-iodide or Fe(CN)3 and PEGylated protein to form a compound need to get rid of other proteins prior to detect, and sensitivity of this method is relatively low, only reach about 1-5 μg/ml. (c) To detect PEG by isotope labeling PEGylated molecule. Although the sensitivity for this method is good, this method can not be used in every PEGylated molecule. Besides, due to the production of radioactive waste, this method can only be performed by specific operators in specific lab, causing inconvenience and leading to unpopularity. Therefore, developing a method which is simple, sensitive, cheap, and able to detect the pharmacokinetics of any PEGylated molecules in vivo can solve those problems caused by traditional methods, such as inconvenience, low sensitivity, and expensive. Also, this new method can be used in any labs, helping labs to evaluate the pharmacokinetics of PEGylated molecules in vivo or in vitro. This method will play an important role in developing PEGylated drug in the future.

SUMMARY OF THE INVENTION

The present invention provides a method for preparing an isolated eukaryotic cell which stably or transiently expresses a functional anti-PEG antibody on a surface of the cell. The present invention also provides a method for a quantitative analysis of a PEG by the isolated eukaryotic cell.

BRIEF DESCRIPTION OF THE DRAWINGS

FIG. 2.

FIG. 3. The sandwich ELISA based on 3T3/AGP3 platform can sensitively detect (FIG. 3A) free PEG molecules up to 100 ng/ml, (FIG. 3B) PEG-Interferon 2α up to 10 ng/ml, (FIG. 3C) Lipo-Dox up to 10 ng/ml, and (FIG. 3D) PEG-Q-dot up to 0.1 nM; and 3T3/DNS is the negative control.

FIG. 4. The sandwich ELISA based on 3T3/15-2 platform is more sensitive in detecting free methoxyl-PEG (CH3O end) molecule than 3T3/AGP3; (FIG. 4A) 5KDa, (FIG. 4B) 2KDa; and 3T3/DNS is the negative control.

FIG. 5. The competitive ELISA is based on 3T3/AGP3 platform.

FIG. 6. The expression level and function of E11, 3-3 and 6-3 cell membrane antibodies are shown. Tests of the protein expression level of anti-PEG membrane antibodies on the 3T3 cells with anti-HA antibody (solid line) and tests of the function of anti-PEG membrane antibody to recognize PEG with PEG-Q-dot (dotted line) are shown. (FIG. 6A) 3T3/E11, (FIG. 6B) 3T3/3-3, (FIG. 6C) 3T3/6-3. The result shows that those three cell lines are able to bind PEG effectively. The result also shows that the sandwich ELISA and the competitive ELISA can use those three cell lines as a platform to detect free PEG molecules and PEGylated macromolecules.

FIG. 7. Detection of CH3O-PEG or CH3O-PEGylated molecules by 15-2 antibody-based or 3T3/15-2 cell-based sandwich ELISA is shown. Sandwich ELISA, with (FIG. 7A) 15-2b or (FIG. 7B) 3T3/15-2 cell as the captured reagent, was used to measure the concentration of CH3O-PEG, including CH3O-PEG$_{20K}$ (●), CH3O-PEG$_{5K}$ (■), CH3O-PEG$_{2K}$ (▲), CH3O-PEG$_{1K}$ (▼), and Lipo-Dox (○).

FIG. 8. Binding of biotinylated PEG and PEG$_{5K}$-$^{131}$I by the AGP3 antibody-based and 3T3/AGP3 cell-based ELISA is shown.

DETAILED DESCRIPTION OF THE INVENTION

In this invention, anti-PEG antibodies or anti-methoxyl-PEG (anti-CH3O-PEG) antibodies are expressed on cell surface which can collocate with a biotinylated anti-PEG antibody (AGP4-Biotin) or biotinylated PEG (PEG-Biotin) to develop a cell-based sandwich ELISA or a cell-based competitive ELISA, respectively. Both of these two methods can sensitively quantify free PEG and PEGylated macromolecules (proteins, nanoparticles and liposomes) as sensitive as nano-gram level. Compared to the traditional ELISA which directly recognizes antibody protein, the cell-based ELISA has several advantages, such as: (1) because of the high growing rate of 3T3 cells, only small amount of serum (or even no serum) is needed for culturing the cells to obtain great amount of cells which present anti-PEG antibody on cell membrane. (2) the antibody presenting on the cell membrane is in a consistent direction, and the anti-PEG antibody has extracellularly presented antigen binding domains, which can effectively improve the sensitivity of detecting PEG. (3) the size of the anti-PEG antibody presenting 3T3 cell is similar to microparticle, which can effectively increase the surface for reaction to improve the sensitivity of detecting PEG.

The present invention relates to a detection kit for detecting polyethylene glycol (PEG), which comprises an anti-PEG antibody presenting cell which presents the anti-PEG antibody on its membrane, wherein the antibody is presented in a consistent direction on the membrane. The present invention also relates to a detection method for detecting PEG. There are two ways to detect PEG: The first way is fixing a cell which presents the anti-PEG antibody on its membrane on a steady holder, and then sequentially adding analyte PEG or PEGylated molecules, chemically modified anti-PEG antibody, and color reagents. The PEG concentration can be quantified by observing color intensity after washing out the remaining color reagent. The second way is fixing a cell which presents the anti-PEG antibody on its membrane on a steady holder, and then adding equal volume of biotinylated PEG and analyte PEG or PEGylated molecules at the same time. Finally, adding color reagent and washing out the remaining color reagent and quantifying the concentration of PEG by the color intensity.

Figure 1:
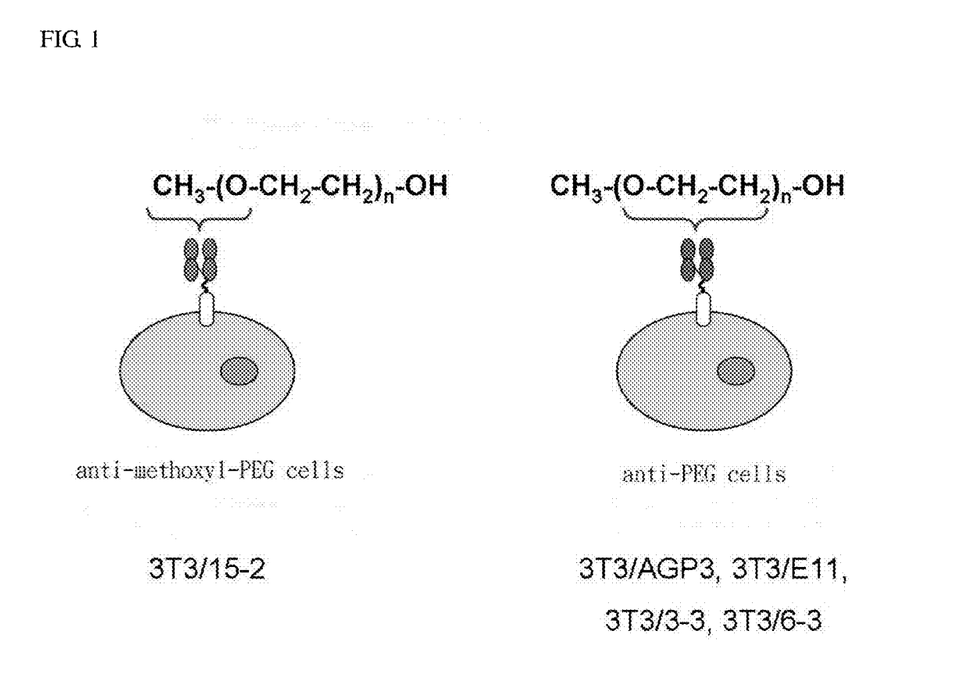
FIG. 1. 3T3/AGP3, 3T3/E11, 3T3/3-3 and 3T3/6-3 cells can recognize the repeat sequence of PEG (—O—CH2—CH2-)n, while 3T3/15-2 cells can recognize the methoxyl-PEG (CH3O-PEG). Therefore, any free PEG molecules and PEGylated macromolecules (e.g. liposome, protein, nano particle, drug, etc.) can be recognized by such kind of cells.
Figure 2A:
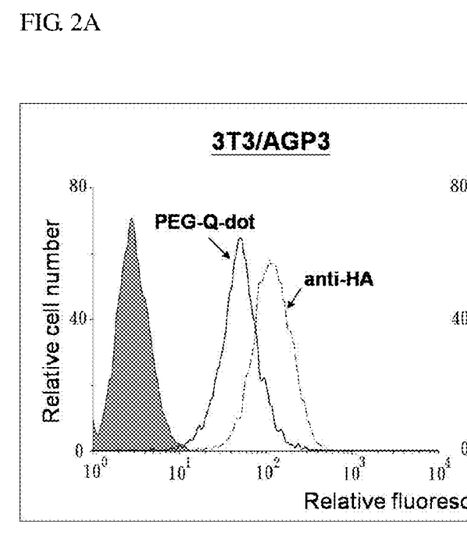
FIG. 2A shows the detection of the expression level of membrane protein antibodies presented on the 3T3/AGP3 cells with HA (hemagglutinin) antibody and the test of the function of AGP3 cell membrane antibodies to recognize PEG with PEG-Q-dot.
Figure 2B:
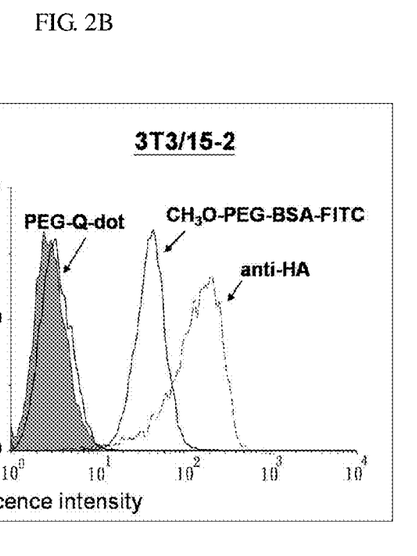
FIG. 2B shows the detection of the expression level of membrane protein antibodies presented on the 3T3/15-2 cells with HA (hemagglutinin) antibody and the test of the function of 15-2 cell membrane antibodies to recognize CH3O-PEG with PEG-Q-dot or CH3O-PEG-BSA-FITC. The result shows that both AGP3 and 15-2 cell membrane antibodies can be highly expressed on the surface of 3T3 cells; 3T3/AGP3 cells can recognize the backbone of PEG, while 3T3/15-2 cells can only recognize the methoxyl-PEG (CH3O-PEG) but not the PEG-Q-dot (PEG without methoxyl).
Figure 3A:
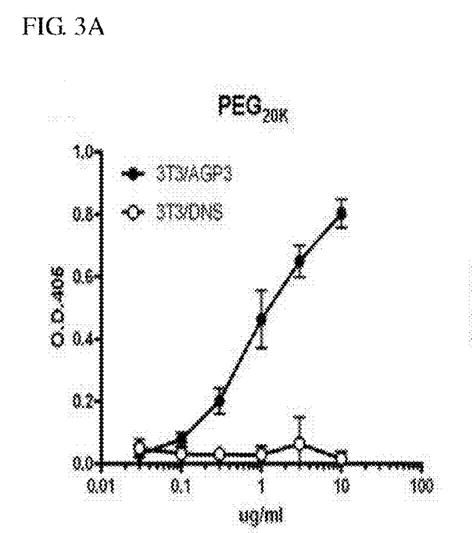
Figure 3B:
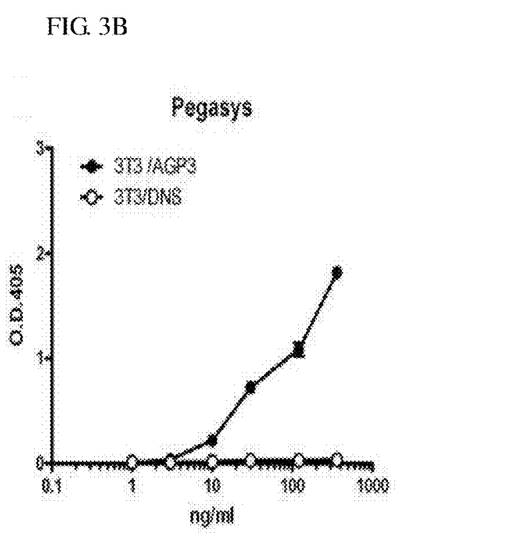
Figure 3C:
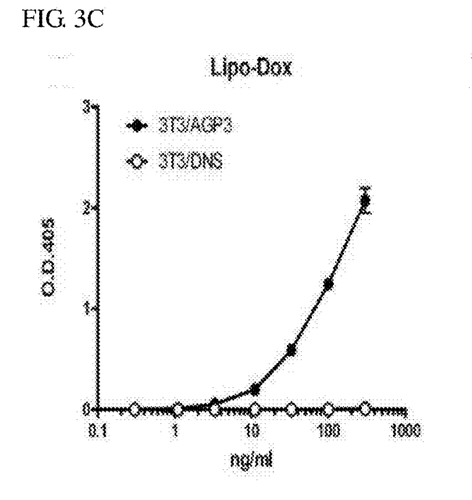
Figure 3D:
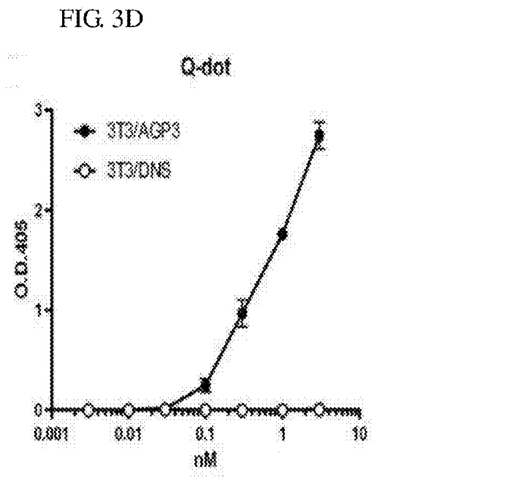

This invention presents all kinds of anti-PEG antibodies (AGP3/IgM, E11/IgG1, 3-3/IgG1, 6-3/IgG1) or an anti-methoxyl-PEG antibody (15-2/IgG2b) to the cell membrane of mammalian cells, such as mouse embryonic fibroblast cells (3T3) to construct a cell line able to quantify all kinds of PEG and PEGylated molecules. In one embodiment of the present invention: (1) The light chain (VL-CK) and heavy chain (VH-CH1) of Fab antibody sequence of the AGP3 antibody or the 15-2 antibody are connected with the foot-and-mouth virus 2A peptide and further combined with the immunoglobulin C2-type extracellular-transmembrane-cytosolic domains of mouse B7 antigen. (2) Afterward, integrating (1) to the virus vector pLNCX to make a pLNCX-AGP3 Fab-B7 and a pLNCX-15-2 Fab-B7 plasmid, respectively. (3) GP2-293 cells infected with said plasmid and pVSVG vector (a retro virus which leads to defects on reproduction for GP2-293) by lipofectamine 2000. 48 hours later, the medium of GP2-293 has retro virus particles which contain AGP3 Fab-B7 gene and 15-2 Fab-B7 gene, respectively. (4) 3T3 cell line is infected with said retro virus particles and infected cells are selected with antibiotics G418 sulfate. (5) At last, those high expression cells are collected by flow cytometry, and then the 3T3/AGP3 cells and 3T3/15-2 cells are obtained. (FIGS. 2A and 2B). A sandwich ELISA can be established by using 3T3/AGP3 cells or 3T3/15-2 cells with biotinylated anti-PEG antibody (AGP4-Biotin). In one embodiment of the present invention, 3T3/AGP3 cells are seeded into a 96 well plate before the PEG or PEGylated macromolecules is added, and then a biotinylated anti-PEG antibody is added as a detecting antibody. Finally, streptavidin-HRP is added. After adequate washing, the concentration of PEG or PEGylated molecules can be known by observing the color intensity of the matrix coated on the 96 well plate. The 3T3/AGP3 cell-based sandwich ELISA can effectively quantify free PEG molecules having molecule weight 20KD (sensitivity up to 100 ng/ml) (FIG. 3A), PEGylated Interferon (PEG-Interferon 2a, Pegasy) (sensitivity up to 10 ng/ml) (FIG. 3B), PEGylated liposomal drug (Lipo-Dox) (sensitivity up to 10 ng/ml) (FIG. 3C), and PEGylated fluorescence nanoparticle (PEG-Quantum dots, PEG-Q-dot) (sensitivity up to 0.1 nM) (FIG. 3D). More importantly, comparing to 3T3/AGP3 cells, the 3T3/15-2 cell-based sandwich ELISA can quantify the free PEG molecules which have methoxyl group more sensitively.

Figure 4A:
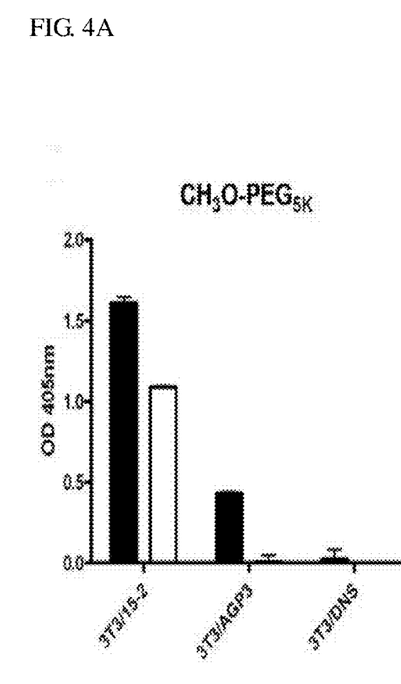
Figure 4B:
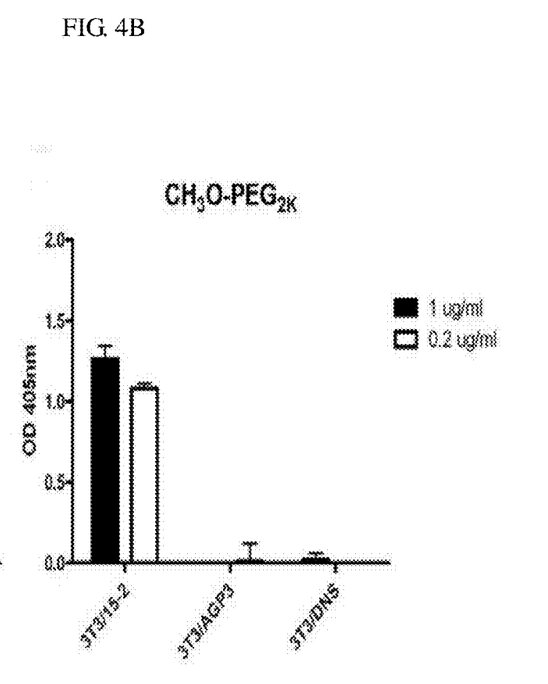
Figure 5A:
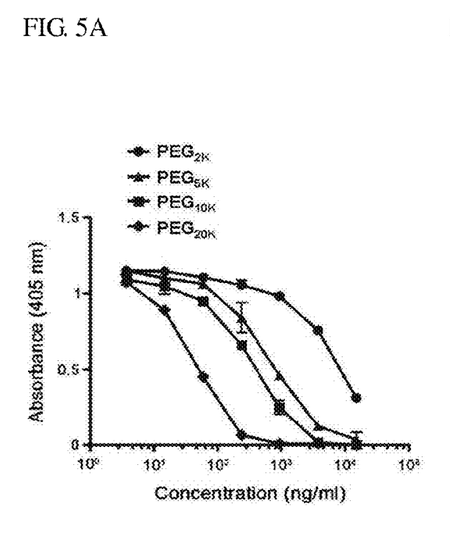
FIG. 5A shows that different concentrations and different molecular weight (MW: 2, 5, 10 and 20KDa) of free PEG molecules compete with biotinylated PEG (125 ng/ml) and the light absorbance shows a linear decrease as the concentration of free PEG molecules (2, 5, 10 and 20KDa) is increased up to 58.6, 14.6, 3.7 and 3.7 ng/ml, respectively. It proves that the competitive ELISA effectively quantifies free PEG molecules and its sensitivity is up to ng/ml scale.
Figure 5B:
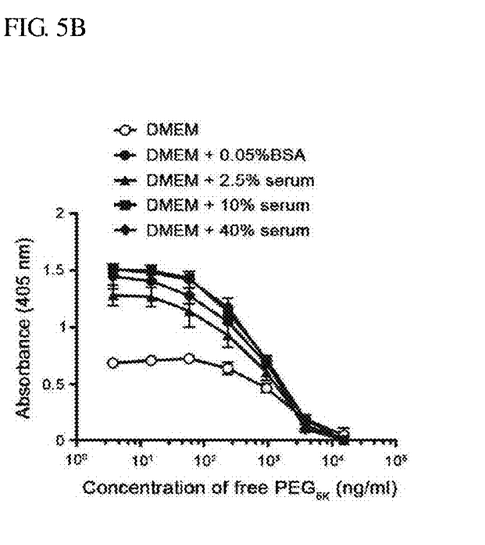
FIG. 5B shows that PEG-Biotin and free PEG molecules (MW: 5KDa) in the solution with different serum concentrations (2.5%-40%) are prepared and the competitive ELISA is performed. The result shows that even when the percentage of serum is as high as 40%, the ability of the competitive ELISA to quantify the amount of free PEG molecules is not affected.
Figure 6A:
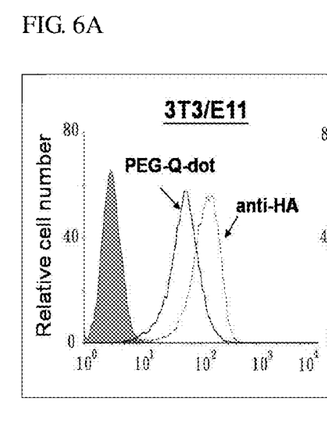
Figure 6B:
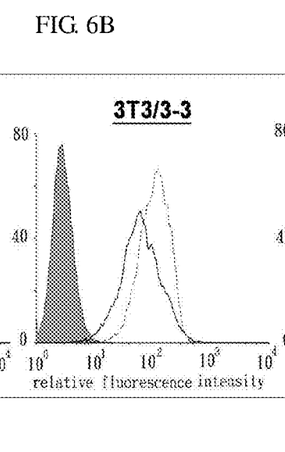
Figure 6C:
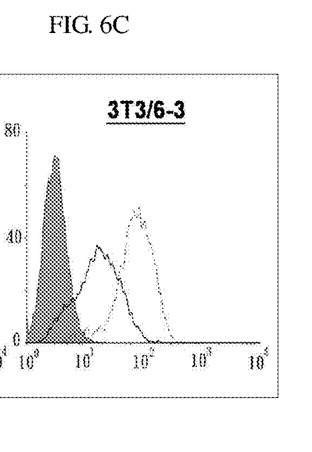

The present invention finds that, comparing to 3T3/AGP3 cells, the sandwich ELISA based on 3T3/15-2 cells can more sensitively quantify free methoxyl-PEG. For the methoxyl-PEG with molecular weight 5,000 and 2000, the detection sensitivity of 3T3/15-2 cell-based sandwich ELISA is respectively 3.7 times and 100 times higher than 3T3/AGP3 cell-based sandwich ELISA do (FIGS. 4A and 4B). Besides, for quantification of non-methoxyl PEG molecules, the present invention collocates 3T3/AGP3 cells which detect PEG backbone with biotinylated PEG to develop a competitive ELISA. Competitive ELISA can be applied by mixing equal volume of biotinylated PEG with the PEG sample, or PEGylated molecules which have different molecular weights (MW: 2K-20KDa). The competitive ELISA can sensitively quantify free PEG molecules with MW 2KDa, 5KDa, 10KDa and 20KDa. The sensitivity is up to 58.6, 14.6, 3.7, and 3.7 ng/ml, respectively (FIG. 5A), and is not influenced by serum (FIG. 5B). The present invention also constructs other cell lines which present anti-PEG antibodies on their cell membranes, such as 3T3/E11 cells, 3T3/3-3 cells and 3T3/6-3 cells (FIGS. 6A-6C). These cell lines can be applied on a sandwich ELISA or a competitive ELISA as well.

The present invention provides a method for preparing an isolated eukaryotic cell which presents an anti-polyethylene glycol (PEG) antibody on a cell membrane, comprising: (a) providing a vector comprising a nucleic acid sequence for encoding an anti-PEG antibody and a nucleic acid sequence for encoding a transmembrane protein; (b) transfecting the vector into an eukaryotic cell; and (c) isolating the eukaryotic cell which presents an anti-PEG antibody on the cell membrane, wherein the anti-PEG antibody presents in a consistent direction on the cell membrane and the anti-PEG antibody has an extracellularly presented antigen binding domain.

In one embodiment, the eukaryotic cell is selected from the group consisting of insect cells, amphibian cells, yeast cells, worm cells, and mammalian cells. Preferably, the eukaryotic cell is a mammalian cell. More preferably, the eukaryotic cell is a 3T3 cell.

The term "vector" is used herein to refer to a nucleic acid molecule having nucleic acid sequences that enables its replication in a host cell. A vector can also include nucleic acid sequences to permit ligation of nucleic acid sequences within the vector, wherein such nucleic acid sequences are also replicated in a host cell. Representative vectors include plasmids, cosmids, and viral vectors. Preferably, the vector is a viral vector. A vector can also mediate recombinant production of an antibody fragment of the anti-PEG antibody.

As used herein, the transmembrane protein is a protein that goes from one side of a membrane through to the other side of the membrane. The function of the transmembrane protein is the gateway or the "loading docks" to deny or permit the transport of specific substances across the biological membrane, to get into the cell, or out of the cell as in the case of waste byproducts. In one embodiment, the transmembrane protein is a protein having a function for carrying and fixing the antibody or antibody fragment on the surface of the cell membrane. In a preferred embodiment, the transmembrane protein fixes the antibody presenting in a consistent direction on the cell and causes that the anti-PEG antibody having an extracellularly presented antigen binding domain. In a more preferred embodiment, the transmembrane protein is a transmembrane protein of B7.

"Host cell" means a cell that contains an expression vector and supports the replication or expression of the expressed vector. Host cells may be prokaryotic cells such as E. coli, or eukaryotic cells such as yeast, insect, amphibian, worm or mammalian cells such as 3T3 cell and the like, e.g., cultured cells, explants, and cells in vivo.

The term "nucleic acid" or "nucleic acid sequences" refers to a deoxyribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones "Antibody" refers to a polypeptide comprising a framework region from an immunoglobulin gene or a fragment thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Preferable, the terms "light chain variable region" (VL) and "heavy chain variable region" (VH) refer to these light and heavy chains respectively.

An antibody includes, but is not limited to, a traditional antibody, a fragment of a traditional antibody containing an antigen binding site, a recombinant antibody containing an antigen binding site, a protein which binds to an antigen, and a product comprising crosslinking any two or more of the above.

In one embodiment, the nucleic acid sequence for encoding the anti-PEG antibody comprises at least a nucleic acid sequence of a heavy chain variable region (VH) and a nucleic acid sequence of a light chain variable region (VL). Preferably, the nucleic acid sequence for encoding the anti-PEG antibody is selected from the group consisting of (a) a AGP3 antibody which is encoded by a nucleic acid sequence of SEQ ID NO: 1 of VH and a nucleic acid sequence of SEQ ID NO: 2 of VL; (b) a E11 antibody which is encoded by a nucleic acid sequence of SEQ ID NO: 3 of VH and a nucleic acid sequence of SEQ ID NO: 4 of VL; (c) a 3-3 antibody consisting of a VH which is encoded by SEQ ID NO: 5 and a VL which is encoded by SEQ ID NO: 6; (d) a 6-3 antibody consisting of a VH which is encoded by SEQ ID NO: 7 and a VL which is encoded by SEQ ID NO: 8; and (e) a 15-2 antibody consisting of a VH which is encoded by SEQ ID NO: 9 and a VL which is encoded by SEQ ID NO: 10.

In another embodiment, the nucleic acid sequences for encoding VL and VH of the vector are connected by a linker. Preferable, the linker is an internal ribosome entry site (IRES) or a virus peptide. More preferable, the virus peptide is a foot-and-mouth virus 2A peptide (FMDV 2A).

As used herein, an "anti-PEG" antibody is an antibody or antibody fragment that specifically binds a polypeptide or protein encoded by an anti-polyethylene glycol (PEG) gene, cDNA, or a subsequence or variant thereof. In one embodiment, the anti-PEG antibody comprises an antigen binding domain. Preferable, the antigen binding domain comprises a VH fragment, a VL fragment or a combination thereof. More preferable, the antigen binding domain comprises a VH fragment and a VL fragment.

As used herein, the term "PEG" comprises a PEG molecule or a PEG-modified molecule. In another embodiment, the anti-PEG antibodies comprising the AGP3 antibody, the E11 antibody, the 3-3 antibody, the 6-3 antibody and the 15-2 antibody are able to detect the PEG. In a preferred embodiment, the 15-2 antibody is capable of detecting a methoxyl end of a methoxyl-PEG.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The present invention also provides a method for a quantitative analysis of a polyethylene glycol (PEG), comprising: (a) providing an eukaryotic cell which presents an anti-PEG antibody on a cell membrane, wherein the anti-PEG antibody presents in a consistent direction on the cell membrane and the anti-PEG antibody has an extracellularly presented antigen binding domain; (b) contacting the eukaryotic cell with a specimen containing PEG; and (c) measuring a concentration of the PEG in the specimen by detecting interaction of the PEG of the specimen and the anti-PEG antibody of the eukaryotic cell.

In one embodiment, the eukaryotic cell is selected from the group consisting of insect cells, amphibian cells, yeast cells, worm cells, and mammalian cells. Preferably, the eukaryotic cell is a mammalian cell. More preferably, the eukaryotic cell is a 3T3 cell.

In one embodiment, the eukaryotic cell comprises a vector comprising a nucleic acid sequence for encoding an anti-PEG antibody and a nucleic acid sequence for encoding a transmembrane protein. Preferably, the nucleic acid sequence for encoding the anti-PEG antibody comprises at least a nucleic acid sequence of a heavy chain variable region (VH) and a nucleic acid sequence of a light chain variable region (VL). More preferably, the nucleic acid sequence for encoding an anti-PEG antibody is selected from the group consisting of (a) a AGP3 antibody which is encoded by a nucleic acid sequence of SEQ ID NO: 1 of heavy chain variable region (VH) and a nucleic acid sequence of SEQ ID NO: 2 of light chain variable region (VL); (b) a E11 antibody which is encoded by a nucleic acid sequence of SEQ ID NO: 3 of VH and a nucleic acid sequence of SEQ ID NO: 4 of VL; (c) a 3-3 antibody consisting of a VH which is encoded by SEQ ID NO: 5 and a VL which is encoded by SEQ ID NO: 6; (d) a 6-3 antibody consisting of a VH which is encoded by SEQ ID NO: 7 and a VL which is encoded by SEQ ID NO: 8; and (e) a 15-2 antibody consisting of a VH which is encoded by SEQ ID NO: 9 and a VL which is encoded by SEQ ID NO: 10.

In one embodiment, the anti-PEG antibody is an antibody or antibody fragment that specifically binds a polypeptide or protein encoded by an anti-polyethylene glycol (PEG) gene, cDNA, or a subsequence or variant thereof. In a preferred embodiment, the anti-PEG antibody is selected from the group consisting of (a) the AGP3 antibody consisting of a heavy chain variable region (VH) which is encoded by SEQ ID NO: 1 and a light chain variable region (VL) which is encoded by SEQ ID NO: 2; (b) the E11 antibody consisting of a VH which is encoded by SEQ ID NO: 3 and a VL which is encoded by SEQ ID NO: 4; (c) the 3-3 antibody consisting of a VH which is encoded by SEQ ID NO: 5 and a VL which is encoded by SEQ ID NO: 6; (d) the 6-3 antibody consisting of a VH which is encoded by SEQ ID NO: 7 and a VL which is encoded by SEQ ID NO: 8; and (e) the 15-2 antibody consisting of a VH which is encoded by SEQ ID NO: 9 and a VL which is encoded by SEQ ID NO: 10.

In another embodiment, the anti-PEG antibody comprises an antigen binding domain. Preferable, the antigen binding domain comprises a VH fragment, a VL fragment or a combination thereof. More preferable, the antigen binding domain comprises a VH fragment and a VL fragment.

In one embodiment, the transmembrane protein is a transmembrane protein of B7. In another embodiment, the vector is a viral vector.

In one embodiment, the PEG comprises PEG molecule or a PEG-modified molecule. In another embodiment, the anti-PEG antibodies comprising AGP3, E11, 3-3 and 6-3 and 15-2 are able to detect the concentration of PEG. In a preferred embodiment, the 15-2 antibody is capable of detecting a methoxyl end of a methoxyl-PEG.

In one embodiment, the detecting interaction of the PEG of the specimen and the anti-PEG antibody of the eukaryotic cell is performed by incubating with a detection agent. Preferably, the detecting interaction of the PEG of the specimen and the anti-PEG antibody of the eukaryotic cell comprises use of a fluorescent, a chemical, a radiological, or enzymatic reporter molecule.

The term "detection agent" refers to an agent that is used to detect an antigen or antibody. A detection agent can be either an "antigen" or an "antibody." A detection agent can be either a labeled "antigen" or "antibody" or an unlabeled "antigen" or "antibody." Suitable labeling methods that can be used in the present invention include, without limitation, isotope labeling, chemical modification, enzyme conjugation, fluorescent dye labeling, luminescence and other labeling methods commonly known by those skilled in the art. Therefore, a detection agent includes, but is not limited to, a chemical molecule, a peptide molecule, a protein molecule, an RNA molecule, a DNA molecule, a traditional antibody, a fragment of a traditional antibody containing an antigen binding site, a recombinant antibody containing an antigen binding site, a protein which binds to an antigen, a bacterial cell, a viral particle, a cell, a particle, and a product comprising crosslinking any two or more of the above.

A detection agent can be in a pure form, or it can be an impure form (e.g., contained in a mixture with other compounds or materials). A detection agent can be in a modified form or can be an unmodified form. According to the order of a "detection agent" used in a method, a "detection agent" can be referred as "a primary detection agent," "secondary detection agent," "a tertiary detection agent" or "a fourth detection agent," and the like.

In another embodiment, the measuring step of (c) comprises immunocytochemistry, enzyme-linked immunosorbent assay (ELISA), fluorescence-activated cell sorting (FACS), multiplex ligand binding or radioimmunoassay. In a preferred embodiment, the ELISA comprises an indirect ELISA, a sandwich ELISA, or a competitive ELISA.

In one embodiment, the eukaryotic cell is fixed in a multi-well plate. In another embodiment, the eukaryotic cell is adhered to a substrate.

The present invention further provides an assay kit for the quantification of polyethylene glycol (PEG), comprising: (a) an eukaryotic cell that stably or transiently expresses at least one anti-PEG antibody on a cell membrane, wherein the anti-PEG antibody presents in a consistent direction on the cell membrane and the anti-PEG antibody has an extracellular presented antigen binding domain; and (b) a ligand or reagent that provides for the detection of the PEG.

In one embodiment, the eukaryotic cell is selected from the group consisting of insect cells, amphibian cells, yeast cells, worm cells, and mammalian cells. Preferably, the eukaryotic cell is a mammalian cell. More preferably, the eukaryotic cell is a 3T3 cell.

In one embodiment, the eukaryotic cell comprises a vector comprising a nucleic sequence for encoding an anti-PEG antibody and a nucleic acid sequence for encoding a transmembrane protein. In a preferred embodiment, the nucleic acid sequence for encoding an anti-PEG antibody is selected from the group consisting of (a) a AGP3 antibody which is encoded by a nucleic acid sequence of SEQ ID NO: 1 of heavy chain variable region (VH) and a nucleic acid sequence of SEQ ID NO: 2 of light chain variable region (VL); (b) a E11 antibody which is encoded by a nucleic acid sequence of SEQ ID NO: 3 of VH and a nucleic acid sequence of SEQ ID NO: 4 of VL; (c) a 3-3 antibody consisting of a VH which is encoded by SEQ ID NO: 5 and a VL which is encoded by SEQ ID NO: 6; (d) a 6-3 antibody consisting of a VH which is encoded by SEQ ID NO: 7 and a VL which is encoded by SEQ ID NO: 8; and (e) a 15-2 antibody consisting of a VH which is encoded by SEQ ID NO: 9 and a VL which is encoded by SEQ ID NO: 10.

In one embodiment, the "PEG" comprises PEG molecule or a PEG-modified molecule. In another embodiment, the anti-PEG antibodies comprising AGP3, E11, 3-3 and 6-3 and 15-2 are able to detect the concentration of PEG. In a preferred embodiment, the 15-2 antibody is capable of detecting a methoxyl end of a methoxyl-PEG.

The present invention mainly provides a cell-based assay for quantifying PEG molecule, wherein the assay comprises fixing an eukaryotic cell that stably or transiently expresses at least one functional anti-PEG antibody that functionally couples with PEG, e.g. a PEG molecule or a PEG-modified molecule, on a substrate, i.e., multi-well plate; contacting said eukaryotic cell with a sample, and assaying the PEG concentration of the sample. Further, the PEG-quantification of the cell-based assay in the present invention that differs from conventional antibody-based assay in that said anti-PEG antibody expressing cell makes the anti-PEG antibody of the cell surface unidirectional organization and expresses a larger contacting surface area as compared to a flat-bed well. Thus, the present invention could obviously increase the sensitivity for quantifying PEG to the nano-gram level.

EXAMPLE

The examples below are non-limiting and are merely representative of various aspects and features of the present invention.

Example 1

Anti-PEG cells were used as a platform to establish a sandwich ELISA to quantify free PEG molecules and PEGylated molecules. 3T3/AGP3 cells were seeded into a 96 wells plate before the PEG or PEGylated molecules were added, and then a biotinylated anti-PEG antibody (AGP4-Biotin) was used as a detecting antibody. Finally, color reagent, streptavidin-HRP, was added into the 96 wells plate. After adequate washing, the concentration of PEG or PEGylated molecules were known by observing the color intensity of the matrix coated on the 96 wells plate. With existence of serum, this method could quantify PEG molecules and PEGylated macromolecules (such as protein, fluorescent-nanoparticle and liposome) with PEG molecular weight 2,000, respectively, and the sensitivity was up to 100 ng/ml (5 nM), 10 ng/ml, 0.1 nM and 10 ng/ml, respectively. Therefore, this method could sensitively quantify all kinds of PEGylated molecules.

Example 2

Anti-methoxyl-PEG cells were used as a platform to establish a sandwich ELISA to quantify all kinds of free methoxyl-PEG molecules. 3T3/15-2 cells were seeded into a 96 wells plate. After that, the methoxyl-PEG was added as an analyte, and then a biotinylated anti-PEG antibody (AGP4-Biotin) was used as a detecting antibody. Finally, streptavidin-HRP was added into the 96 wells plate. After adequate washing, the concentration of methoxyl-PEG was known by observing the color intensity of the matrix coated on the 96 wells plate. With existence of serum, this method can quantify all kinds of free methoxyl-PEG molecules ($CH_3O$-PEG2K and $CH_3O$-PEG5K), and the sensitivity was better than using 3T3/AGP3 platform. Therefore, the sandwich ELISA method using 3T3/15-2 platform can sensitively quantify all kinds of methoxyl-PEG molecules.

Example 3

Anti-PEG cells were used as a platform to establish a competitive ELISA to quantify free PEG molecules. 3T3/AGP cells were seeded into a 96 wells plate, and a fixed amount of the biotinylated-PEG molecule (PEG-Biotin) was mixed with the analyte (free PEG molecule) by equal volume (1:1) to form a mixture, and then the mixture was added into the 96 wells plate. Finally, streptavidin-HRP was added into the 96 wells plate. After adequate washing, the concentration of free PEG molecule can be known by observing the color intensity of the matrix coated on the 96 wells plate. With existence of 40% serum, this method could quantify PEG molecules with molecular weight 20,000 to 2,000 (PEG20K, PEG10K, PEG5K and PEG2K), and the sensitivity was up to 3.7 ng/ml, 3.7 ng/ml, 14.6 ng/ml and 58.6 ng/ml, respectively. Therefore, this platform could sensitively quantify many kinds of free PEG molecules.

Example 4

Development of Surface Anti-PEG (or Anti-CH3O-PEG) Antibody Expressing Cells (1) Plasmid Construction
The light chain variable region (VL) and the heavy chain variable region (VH) domains of the anti-PEG antibodies (AGP3, E11, 3-3, 6-3) or anti-CH3O-PEG antibody (15-2) were cloned from cDNA prepared from the hybridoma. The cloning cDNAs of VL and VH of the antibodies consisted of the following: (a) the AGP3 antibody comprised the SEQ ID NO: 1 of VH and the SEQ ID NO: 2 of VL; (b) the E11 antibody comprised the SEQ ID NO: 3 of VH and the SEQ ID NO: 4 of VL; (c) the 3-3 antibody comprised the SEQ ID NO: 5 of VH and the SEQ ID NO: 6 of VL; (d) the 6-3 antibody comprised the SEQ ID NO: 7 of VH and the SEQ ID NO: 8 of VL; and (e) the 15-2 antibody comprised the SEQ ID NO: 9 of VH and the SEQ ID NO: 10 of VL.

The VL and VH genes, joined by a composite furin-2A protease cleavage site [or an internal ribosome entry site (IBES)], were subcloned into a retroviral vector, pLNCX-eB7, by use of SfiI and SalI restriction sites. The expression vector, pLNCX-α-mPEG-eB7, encodes α-mPEG Fab fused to the immunoglobulin C2-type extracellular-transmembrane-cytosolic domains of the mouse B7-1 antigen. A plasmid (pLNCX-anti-DNS-eB7) that encodes a membrane Fab with specificity for 5-(dimethylamino)naphthalene-1-sulfonyl chloride (DNS) was constructed in an analogous fashion to act as a negative control.

(2) Generation of Surface Anti-PEG (or Anti-CH3O-PEG) Antibody Expressing Cells by Retroviral Transduction
To produce pseudotyped retroviruses, pLNCX-anti-PEG-eB7 or pLNCX-anti-$CH_3O$-PEG-eB7) was cotransfected with pVSVG (Clontech Inc.) to GP2-293 cells by Lipofectamine 2000 (Invitrogen Inc.). Two days after transfection, the culture medium was filtered and mixed with 8 μg/mL Polybrene (Sigma-Aldrich Inc.), and the mixture was added to BALB/3T3 cells. Following retroviral transduction, cells were selected in G418-containing medium and sorted on a FACS Cantor (BD Biosciences Inc.) to generate 3T3/AGP3, 3T3/E11, 3T3/3-3, 3T3/6-3, and 3T3/15-2 cells, respectively.

Example 5

Figure 7A:
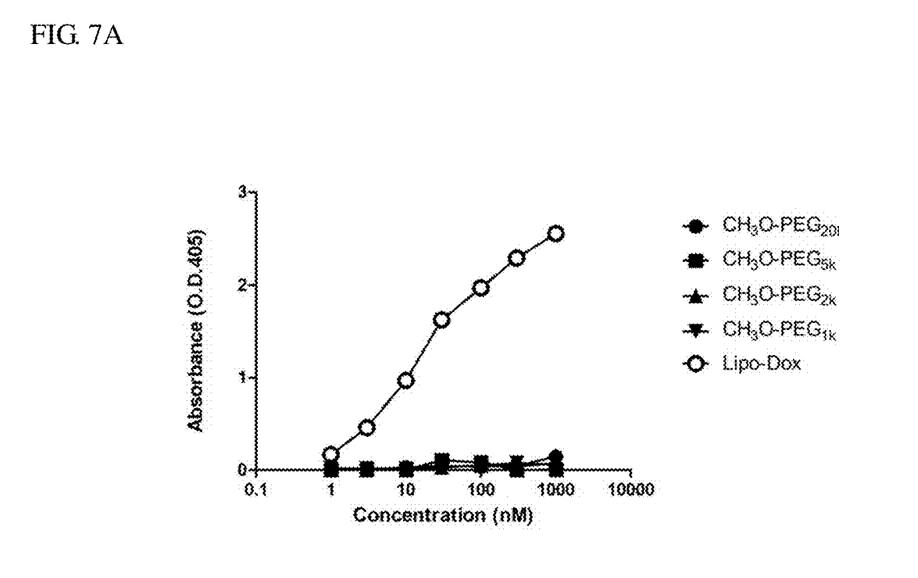
Figure 7B:
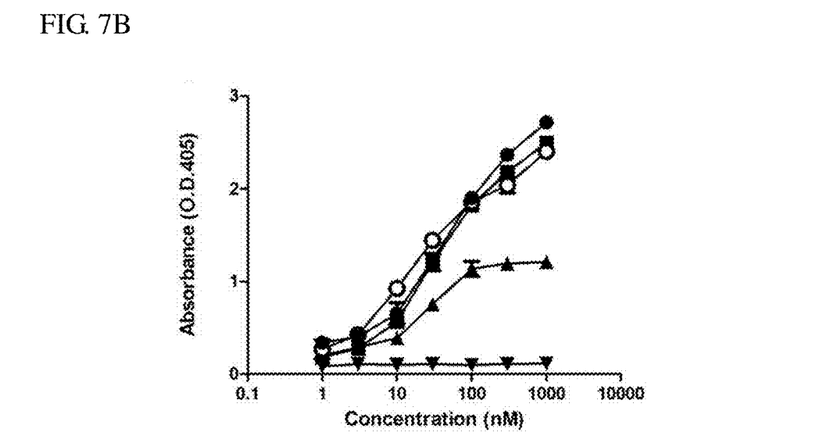

To Compare the Quantative Efficacy of CH3O-PEG or CH3O-PEGylated Molecules by 3T3/15-2 Cell-Based or 15-2 Antibody-Based Sandwich ELISA To test whether 3T3/15-2 cell-based or 15-2 antibody-based sandwich ELISA could be used to quantify $CH_3O$-PEG molecules, $CH_3O$-PEG (1K, 2K, 5K, and 20K Da) or Lipo-Dox (liposomal doxorubicin conjugated with $CH_3O$-$PEG_{2K}$) was added to 3T3/15-2 cell or 15-2 antibody coated 96 well/ plates, respectively. Captured mPEG molecules were then quantified by sequential addition of biotinylated AGP4 antibody (AGP4-biotin), streptavidin-conjugated horseradish peroxidase (streptavidin-HRP) and ABTS substrate. It showed that 3T3/15-2 cell-based and 15-2 antibody-based sandwich ELISA detected Lipo-Dox with similar, apparent avidities (FIGS. 7A and 7B). Only 3T3/15-2 cell-based sandwich ELISA could detect $CH_3O$-PEG molecules above molecular weight of 2000 Da. The sensitivity depended on the length of the PEG chain. $CH_3O$-PEG$_{5K}$ and $CH_3O$-PEG$_{2K}$ could be effectively detected at concentrations as low as 1 nM, respectively. However, $CH_3O$-PEG$_{1K}$ could not be detected by the pairing of 3T3/15-2 cell and AGP4-biotin.

Example 6

Binding of PEG in AGP3 Antibody-Based and 3T3/AGP3 Cell-Based ELISA

Figure 8A:
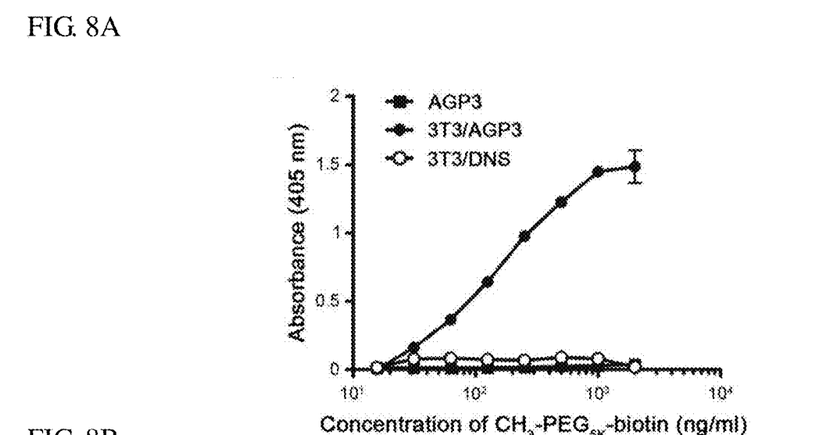
FIG. 8A shows that graded concentrations of PEG$_{5K}$-biotin were added to plate-coated AGP3 antibody (■), 3T3/AGP3 cells (●), or 3T3/DNS cells (○), followed by detection with streptavidin-HRP and ABTS.
Figure 8B:
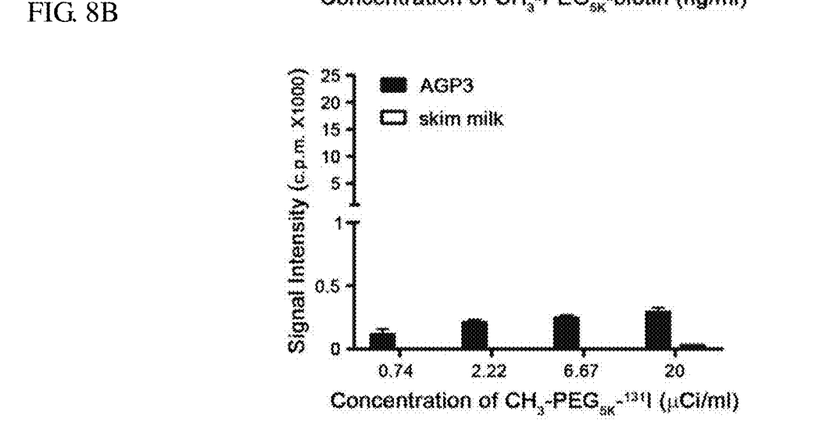
FIG. 8B shows direct binding of PEG$_{5K}$-$^{131}$I by AGP3 antibody-coated plates (solid bars) or skim milk-coated plates (open bars).
Figure 8C:
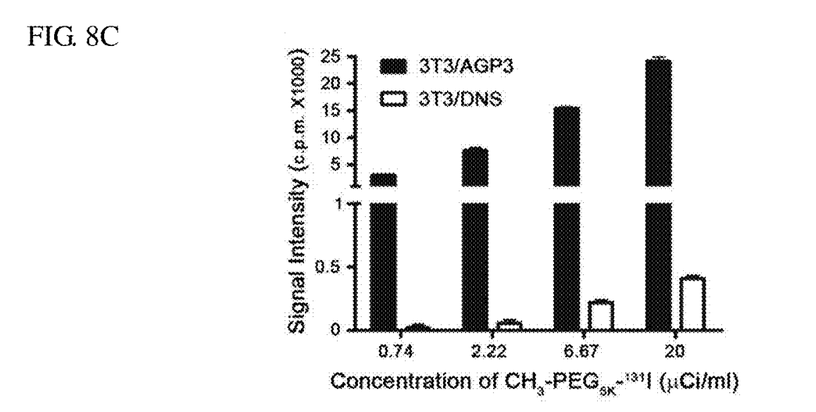
FIG. 8C shows direct binding of PEG$_{5K}$-$^{131}$I by 3T3/AGP3 cell-coated plates (solid bars) or 3T3/DNS cell-coated plates (open bars). (SD values are shown).

To further investigate the potential mechanism that dictates the differential ability in detecting PEG by the cell surface-expressed anti-PEG antibody and coated AGP3 antibody, the present invention compared direct binding of PEG$_{5K}$-biotin (FIG. 8A) or PEG$_{5K}$-$^{131}$I (FIGS. 8B and 8C) to AGP3 antibody and 3T3/AGP3 cells precoated in 96-well plates.
(1) For PEG$_{5K}$-Biotin The 3T3/AGP3 and 3T3/DNS cells ($2\times10^5$ cells/well) were seeded overnight in 96-well plates in culture medium. After extensive washing, captures were fixed by 1% paraformaldehy for 3 min. Plates were blocked with 5% skim milk in PBS for 2 hours at 37° C. PEG$_{5K}$-biotin was serially diluted and added to the cells at room temperature for 1 h. After washing, streptavidin-HRP and ABTS were sequentially added to the plates to quantify the captured PEG$_{5K}$-biotin. Color development was measured at 405 nm on a microplate reader. Using this method, the detection limit of PEG5K-biotin in the 3T3/AGP3 cell-based ELISA was 15.6 ng/mL (FIG. 8A). On the contrary, AGP3 antibody-based ELISA still failed to detect the PEG$_{5K}$-biotin.
(2) For PEG$_{5K}$-$^{131}$I The 3T3/AGP3 and 3T3/DNS cells ($2\times10^5$ cells/well) were seeded overnight in 96-well plates in culture medium. After extensive washing, captures were fixed by 1% paraformaldehy for 3 min. Plates were blocked with 5% skim milk in PBS for 2 hours at 37° C. PEG$_{5K}$-$^{131}$I was serially diluted and added to the cells at room temperature for 1 h. After washing, 1N NaOH was added to elute the bound PEG$_{5K}$-$^{131}$I. The radioactivity of these samples was counted on a γ counter. The present invention found 3T3/AGP3 cells captured significantly more PEG$_{5K}$-$^{131}$I than did coated AGP3 antibody. On average, signal intensity per well was 26.5-fold (3026 vs 114, $p<0.0001$), 36.4-fold (7635 vs 210, $p<0.0001$), 62.7-fold (15 380 vs 245, $p<0.0001$), and 82.3-fold (24 125 vs 293, $p<0.0001$) greater for the 3T3/AGP3 cell-coated plate than for the AGP3 antibody-coated plate after addition of 0.74, 2.22, 6.67, and 20 μCi/mL PEG$_{5K}$-$^{131}$I, respectively (FIGS. 8B and 8C).

Example 7

Figure 9:
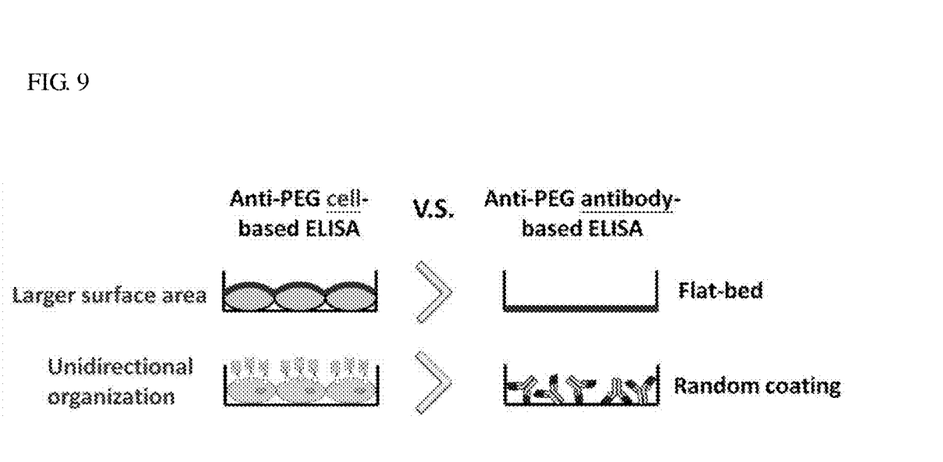
FIG. 9. The comparative analyses of the anti-PEG cell-based ELISA and the anti-PEG antibody-based ELISA are shown.

The Comparative Analysis Showed that the 3T3/AGP3 Cells Captured Significantly More PEG$_{5K}$-Biotin or PEG$_{5K}$-$^{131}$I than Did Coated AGP3 Antibody According to the above experiments, lack of direct binding of PEG$_{5K}$-$^{131}$I by AGP3 antibody-coated plate was surprising and unaccounted for at present, as AGP3 was a monoclonal antibody specific to the PEG backbone. It was unlikely that insufficient AGP3 was coated on microtiter plates to bind PEG$_{5K}$-$^{131}$I, as up to 1 μg of the antibody/well was coated in the plate and this amount of antibody could detect PEGylated macromolecules with high sensitivity (as shown in FIG. 7A). Alternatively, antibodies randomly attached to the plate might be in a disorganized orientation, which could "pull away" among themselves for binding of PEG (which is theoretically a flexible and linear structure), and ultimately decrease avidity. On the contrary, surface AGP3 antibody should display only one organization (outward-pointing) after coating the 3T3/AGP3 cells to the plate. In addition, 3T3/AGP3 cells might be considered to be analogous to microbeads, which had been shown to increase immobilization of capture antibodies in assay plates due to a larger surface area as compared to a flat-bed well, thus enhancing assay sensitivity (FIG. 9). The combination of unidirectional organization and a larger surface area on which the surface AGP3 antibody were presented might explain better binding of PEG by a mechanism analogous to the "cooperative binding model".

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The antibodies, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for preparing an isolated eukaryotic cell which presents an anti-polyethylene glycol (PEG) antibody on a cell membrane, comprising:
   (a) providing a vector comprising a nucleic acid sequence for encoding the anti-PEG antibody which is fused thereto a nucleic acid sequence for encoding a transmembrane protein, wherein the nucleic acid sequence for encoding the anti-PEG antibody comprises at least a nucleic acid sequence of a heavy chain variable region (VH) and a nucleic acid sequence of a light chain ion (VL) and the nucleic acid sequence for encoding the anti-PEG antibody is selected from the group consisting of (i) a 3-3 antibody consisting of the VH encoded by SEQ ID NO: 5 and the VL encoded by SEQ ID NO: 6; (ii) a 6-3 antibody consisting of the VH encoded by SEQ ID NO: 7 and the VL encoded by SEQ ID NO: 8; (iii) a 15-2 antibody consisting of the VH encoded by SEQ ID NO: 9 and the VL encoded by SEQ ID NO: 10; and combinations thereof;
   (b) transfecting the vector into an eukaryotic cell, thereby enabling the eukaryotic cell to express the anti-PEG antibody and the transmembrane protein; and
   (c) isolating the eukaryotic cell which presents the anti-PEG antibody on the cell membrane, wherein the anti-PEG antibody presents in a consistent direction on the cell membrane and the anti-PEG antibody has an extracellularly presented antigen binding domain.

2. The method of claim 1, wherein the vector is a viral vector.

3. The method of claim 1, wherein the antigen binding domain comprises a VH region and a VL region.

4. The method of claim 1, wherein the transmembrane protein is a transmembrane protein of B7.

5. The method of claim 1, wherein the eukaryotic cell is selected from the group consisting of insect cells, amphibian cells, yeast cells, worm cells, and mammalian cells.

6. The method of claim 1, wherein the 15-2 antibody is capable of detecting a methoxyl end of a methoxyl-PEG.

7. A method for a quantitative analysis of a polyethylene glycol (PEG), comprising:
   (a) providing an isolated eukaryotic cell which presents an anti-PEG antibody on a cell membrane, wherein the anti-PEG antibody presents in a consistent direction on the cell membrane and has an extracellularly presented antigen binding domain, wherein the anti-PEG antibody comprises at least a heavy chain variable region (VH) and a light chain variable region (VL), and the isolated eukaryotic cell comprises a vector comprising a nucleic acid sequence for encoding the anti-PEG antibody which is fused thereto a nucleic acid sequence for encoding a transmembrane protein, and the nucleic acid sequence for encoding the anti-PEG antibody is selected from the group consisting of (i) a 3-3 antibody consisting of the VH encoded by SEQ ID NO: 5 and the VL encoded by SEQ ID NO: 6; (ii) a 6-3 antibody consisting of the VH encoded by SEQ ID NO: 7 and the VL encoded by SEQ ID NO: 8; (iii) a 15-2 antibody consisting of the VH encoded by SEQ ID NO: 9 and the VL encoded by SEQ ID NO: 10; and combinations thereof;
   (b) contacting the anti-PEG antibody on the cell membrane of the eukaryotic cell with a specimen suspected containing a PEG to form a specific binding complex between the anti-PEG antibody and the PEG in the specimen; and
   (c) measuring a concentration of the PEG in the specimen by detecting an amount of the binding complex between the PEG in the specimen and the anti-PEG antibody on the cell membrane of the eukaryotic cell.

8. The method of claim 7, wherein the eukaryotic cell is selected from the group consisting of insect cells, amphibian cells, yeast cells, worm cells, and mammalian cells.

9. The method of claim 7, wherein the PEG comprises a PEG molecule or a PEG-modified molecule.

10. The method of claim 7, wherein the 15-2 antibody is capable of detecting a methoxyl end of a methoxyl-PEG.

11. The method of claim 7, wherein the eukaryotic cell is fixed in a multi-well plate.

12. The method of claim 7, wherein the eukaryotic cell is adhered to a substrate.

13. The method of claim 7, wherein the amount of binding complex of the PEG in the specimen and the anti-PEG antibody on the cell membrane of the eukaryotic cell is detected with a fluorescent, a chemical, a radiological, or an enzymatic reporter molecule.

14. The method of claim 7, wherein the measuring step of (c) comprises immunocytochemistry, an enzyme-linked immunosorbent assay (ELISA), a fluorescence-activated cell sorting (FACS), a multiplex ligand binding assay or a radioimmunoassay.

15. The method of claim 14, wherein the ELISA comprises an indirect ELISA, a sandwich ELISA, or a competitive ELISA.

* * * * *